United States Patent [19]

Noda et al.

[11] Patent Number: 4,770,760
[45] Date of Patent: Sep. 13, 1988

[54] ELECTROCHEMICAL NOx SENSOR

[75] Inventors: Makoto Noda, Nagoya; Nobuhide Kato, Aichi; Hiroshi Kurachi, Konan, all of Japan

[73] Assignee: NGK Insulators, Ltd., Aichi, Japan

[21] Appl. No.: 79,466

[22] Filed: Jul. 30, 1987

[30] Foreign Application Priority Data

Aug. 4, 1986 [JP] Japan ................................ 61-183099

[51] Int. Cl.$^4$ ............................................. G01N 27/46
[52] U.S. Cl. .................................. 204/425; 204/1 T; 204/426; 204/427
[58] Field of Search ............... 204/1 N, 1 T, 421–429; 422/98

[56] References Cited

U.S. PATENT DOCUMENTS

| 3,413,199 | 11/1968 | Morrow | 204/1 B |
| 3,707,455 | 12/1972 | Derr et al. | 204/415 |
| 4,199,425 | 4/1980 | Sinkevitch | 204/195 |
| 4,505,807 | 3/1985 | Yamada | 204/425 |
| 4,568,443 | 2/1986 | Asayama et al. | 204/426 |

FOREIGN PATENT DOCUMENTS 59-91358  5/1984  Japan .

Primary Examiner—T. Tung
Attorney, Agent, or Firm—Parkhurst & Oliff

[57] ABSTRACT

An NOx sensor for determining the concentration of NOx contained in a measurement gas, having first and second electrochemical detecting elements each of which includes an oxygen pumping cell and an oxygen sensing cell. Each of the pumping and sensing cells of the first and second detecting elements consists of a solid electrolyte and a pair of electrodes. At least one of the electrodes of the oxygen pumping and sensing cells of the second detecting elements which are exposed to the introduced measurement gas, is used as a catalytic electrode which is provided with a catalyst for reducing the nitrogen oxides contained in the measurement gas. The second detecting element detects an oxygen partial pressure of the measurement gas while the nitrogen oxides are reduced by the catalyst of the catalytic electrode. The NOx concentration is determined, based on a difference between two outputs of the first and second detecting elements which represent the oxygen partial pressures of respective portions of the measurement gas detected by the first and second detecting elements.

22 Claims, 3 Drawing Sheets

MEASUREMENT GAS
= NO/CO/O$_2$/N$_2$
(CO/NO~1/2 EQUIVALENT)

SHIFT BY ADDITION OF NO$_2$

ELECTROCHEMICAL NOx SENSOR

BACKGROUND OF THE INVENTION

1. Field of the Invention

The present invention relates in general to an NOx sensor, and more particularly to a device suitable for determining the concentration of nitrogen oxides contained in emissions from an internal combustion engine, various burned exhaust gases emitted from heating furnaces and boilers, or anesthetic gases.

2. Discussion of the Prior Art and its Problems

As a device for detecting NOx (oxides of nitrogen) contained in an atmosphere, an NOx sensor operable according to the principle of a concentration cell is proposed. For example, laid-open publication No. 59-91358 (published on May 26, 1984) of Japanese Patent Application discloses a laughing gas sensor which has a catalytic electrode, and U.S. Pat. No. 4,199,425 discloses an oxygen sensor having a porous ceramic coating which is formed on an electrode and which contains rhodium for decomposing NOx of measurement gas.

In the NOx sensors of the concentration cell type indicated above, a relationship between the output (electromotive force) of the sensors and the NOx concentration of a measurement gas is influenced by the oxygen partial pressure of the measurement gas, and is not consistent. Namely, a variation in the output of the sensor responsive to a variation in the NOx concentration is relatively small where the oxygen partial pressure of the measurement gas is comparatively high. Conversely, the variation in the sensor output is relatively large where the oxygen partial pressure of the measurement gas is comparatively low. Therefore, the oxygen partial pressure of the measurement gas must be known, and consequently the determination of the NOx concentration requires the use of a separate sensor for detecting the oxygen partial pressure, in addition to the NOx sensor. Also, it is required to compensate the output of the sensor for a variation in the NOx concentration, depending upon the detected oxygen partial pressure of the measurement gas. Another problem encountered in the known NOx sensor lies in insufficient measuring accuracy or sensitivity of the sensor due to an extremely small variation in the output (electromotive force) of the sensor for a given variation in the NOx concentration, where the oxygen partial pressure of the measurement gas is considerably high. Thus, the known NOx sensors suffer from the problems indicated above.

SUMMARY OF THE INVENTION

The present invention was developed in the light of the foregoing problems experienced in the prior art. It is accordingly an object of the present invention to provide an improved NOx sensor wherein a relationship between the output of the sensor and the NOx concentration of the measurement gas is consistent, irrespective of the oxygen partial pressure of the measurement gas.

The above object may be attained according to the principle of the present invention, which provides an NOx sensor for determining the concentration of nitrogen oxides contained in a measurement gas in an external measurement-gas space, comprising: (1) a first electrochemical oxygen partial pressure detecting element including (a) a first electrochemical oxygen pumping cell having an oxygen-ion conductive solid electrolyte body, and a pair of electrodes, (b) a first electrochemical oxygen sensing cell having an oxygen-ion conductive solid electrolyte body, and a pair of electrodes, (c) first diffusion-resistance means for introducing the measurement gas from the external measurement-gas space, with a first predetermined diffusion resistance, so that one of the pair of electrodes of the first oxygen pumping cell, and one of the pair of electrodes of the first oxygen sensing cell, are exposed to the introduced measurement gas, and (d) first reference-gas inlet means for exposing the other of the pair of electrodes of the first oxygen sensing cell to a reference gas; (2) a second electrochemical oxygen partial pressure detecting element including (i) a second electrochemical oxygen pumping cell having an oxygen-ion conductive solid electrolyte body, and a pair of electrodes, (ii) a second electrochemical oxygen sensing cell having an oxygen-ion conductive solid electrolyte body, and a pair of electrodes, (iii) second diffusion-resistance means for introducing the measurement gas from the external measurement-gas space, with a second predetermined diffusion resistance substantially equal to the first predetermined diffusion resistance, so that one of the pair of electrodes of the second oxygen pumping cell, and one of the pair of electrodes of the second oxygen sensing cell, are exposed to the introduced measurement gas, and (iv) second reference-gas inlet means for exposing the other of the pair of electrodes of the second oxygen sensing cell to a reference atmosphere substantially the same as the reference gas; (3) at least one catalytic electrode which consists of at least one of the above-indicated one electrode of the second oxygen pumping cell and the above-indicated one electrode of the second oxygen sensing cell, which are exposed to a portion of the measurement gas introduced through the second diffusion-resistance means, each catalytic electrode being provided with a catalyst for reducing nitrogen oxides contained in the introduced measurement gas, so that the second electrochemical oxygen partial pressure detecting element detects an oxygen partial pressure of the portion of the measureement gas introduced through the second diffusion-resistance means, while the nitrogen oxides are reduced by the catalyst; and (4) means for determining the concentration of the nitrogen oxides based on a difference between two outputs of the first and second electrochemical oxygen partial pressure detecting elements, the two outputs representing the oxygen partial pressures of the respective portions of the measurement gas introduced through the first and second diffusion-resistance means.

It follows from the above description that the NOx sensor of the present invention includes the two electrochemical oxygen partial pressure detecting elements having a construction similar to that of a known oxygen sensor. One of the two detecting elements, i.e, the first detecting element is adapted to detect the partial pressure of oxygen of the measurement gas in an ordinary manner. The other detecting element, i.e., the second detecting element is adapted to reduce the nitrogen oxides (NOx) contained in the measurement gas, due to a catalytic reaction of the catalytic electrode or electrodes provided with the catalyst for reducing the NOx. Thus, the second detecting element detects the partial pressure of oxygen whose volume is increased as a function of the amount of the NOx reduced by the catalytic electrode or electrodes. Generally, the oxygen partial pressures detected by the first and second electrochemical detecting elements are obtained as pumping currents (Ip) of the oxygen pumping cells of the detecting elements. These pumping currents (Ip) provided as the outputs of the detecting elements are linearly proportional to the oxygen partial pressure of the measurement gas (which includes an increase due to the decomposition of NOx by the catalytic reaction).

In other words, a variation in the outputs (Ip) of the NOx sensor for a given amount of variation in the NOx concentration of the measurement gas is consistent, without being influenced by the oxygen partial pressure of the measurement gas as encountered in a conventional concentration type NOx sensor, even if the oxygen partial pressure of the measurement gas is varied over a relatively wide range. That is, the measuring accuracy or sensitivity of the present NOx sensor is not deteriorated even when the measurement gas has a relatively high oxygen partial pressure. Further, the instant NOx sensor does not require the use of a separate oxygen partial pressure sensor, since the NOx concentration of the measurement gas is determined based on a difference between the outputs of the two electrochemical detecting elements, one of which uses ordinary electrodes made of platinum for example, and the other of which uses at least one electrode provided with the NOx reducing catalyst.

In the case where the measurement gas contains one or more reductive components (including CO, for example), it is also required that the component(s) (CO, etc.) which affect the oxygen partial pressure be known, as previously indicated. Described more specifically, a platinum electrode used in a common oxygen sensor of a concentration cell type has a catalytic function with respect to reductive gas components such as CO. Therefore, the concentration of CO and other reductive components affects the concentration of oxygen in the measurement gas. Thus, the concentration of the components (oxygen and reductive components) in the measurement gas affecting the oxygen partial pressure must be known, in order to compensate the output (electromotive force) of the sensor for an influence of such components.

The above situation does not apply to the NOx sensor of the present invention, in which the first detecting element uses ordinary electrodes such as platinum electrodes, while the second detecting element uses at least one catalytic electrode. The NOx determination is made based on a difference between the two outputs in the form of pumping currents (Ip) obtained from the first and second detecting elements. Although the oxygen partial pressures detected by the two detecting elements are varied with a change in the composition of the measurement gas, the difference between the two outputs representing the oxygen partial pressures (including an increase due to the decomposition of NOx) reflects the NOx concentration of the measurement gas, without an influence of a change in the composition of the measurement gas. Hence, the instant NOx sensor adapted to determine the NOx concentration based on a difference between two outputs (Ip) assures considerably improved sensing accuracy, as compared with a conventional concentration-cell type sensor, even where the measurement gas contains two or more reductive components.

The catalyst may be rhodium cobalt oxide, nickel oxide palladium cerium oxide lanthanum oxide, or similar material, or a mixture thereof. Among these materials, rhodium is particularly preferred for higher catalytic ability, higher stability in the measurement gas, and better adhesiveness to the platinum electrode.

The catalyst may be applied to each catalytic electrode such that the catalytic electrode is impregnated with the catalyst, or coated with a layer of the catalyst. Alternatively, the catalyst may be applied in the form of a layer of the catalyst formed on a ceramic overcoat formed on the electrode. A further alternative method of applying the catalyst is to impregnate such a ceramic overcoat with the catalyst.

According to one feature of the invention, the NOx sensor is constructed such that the first and second electrochemical oxygen partial pressure detecting elements consist of an integrally formed one-piece structure. This construction permits (a) detection of the oxygen partial pressure of the measurement gas by the first detecting element, at a position relativly close to the second detecting element, and (b) minimization of a temperature gradient between the first and second detecting elements, so that the determination of the NOx concentration may be made without a compensation of the sensor output for the temperature gradient. Thus, the integral one-piece structure of the instant NOx sensor assures considerably improved accuracy of measurement of the NOx concentration of the measurement gas. In this case, the first and second diffusion-resistance means, and/or the first and second reference-gas inlet means, are preferably defined by an integral portion or portions of the integrally formed one-piece structure of the sensor.

According to another feature of the invention, at least one of the pair of electrodes of the first oxygen pumping cell is commonly used as at least one of the pair of electrodes of the first oxygen sensing cell. According to a further feature of the invention, at least one of the pair of electrodes of the second oxygen pumping cell is commonly used as at least one of the pair of electrodes of the second oxygen sensing cell.

According to still a further feature of the invention, integrally formed heating means is provided for heating the first and second oxygen pumping and sensing cells of the first and second electrochemical oxygen partial pressure detecting elements. In this case, the pumping and sensing cells are maintained at suitable operating temperatures.

BRIEF DESCRIPTION OF THE DRAWINGS

The foregoing and other objects, features and advantages of the present invention will be better understood by reading the following description of preferred embodiments of the invention, when considered in connection with the accompanying drawings, in which.

DETAILED DESCRIPTION OF THE PREFERRED EMBODIMENTS

To further clarify the concept of the present invention, the several preferred embodiments of the invention will be described in detail, by reference to the accompanying drawings.

Figure 1A:
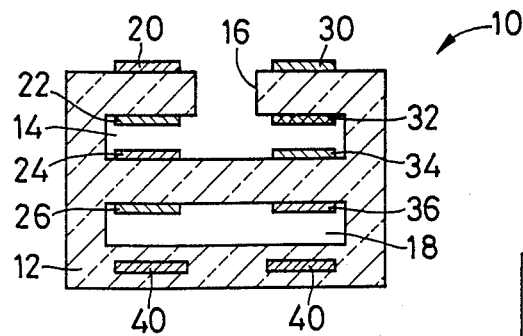
FIG. 1(a) is an elevational view in transverse cross section of a sensing element of one embodiment of an NOx sensor of the present invention, taken along line I—I of FIG. 1(b)
Figure 1B:
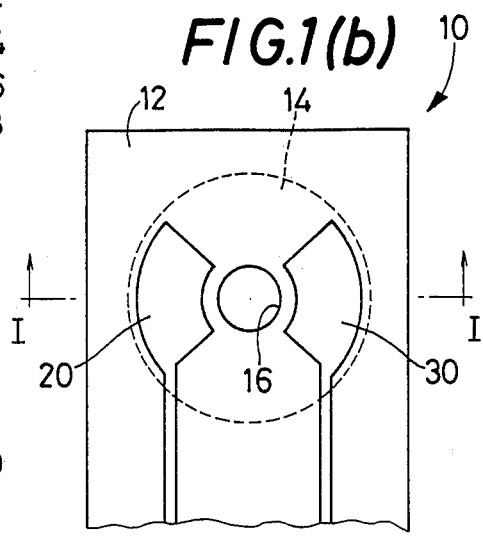
FIG. 1(b) is a fragmentary plan view of the sensing element of FIG. 1(a)

Referring first to FIGS. 1(a) and 1(b), there is shown a sensing element 10 of one embodiment of the NOx sensor of the invention. The sensing element 10 consists of a generally elongate planar structure having a relatively small width. The sensing element 10 incorporates in its distal detecting end portion (one of its opposite longitudinal ends), an integrally formed assembly of a first electrochemical oxygen partial pressure detecting element and a second electrochemical oxygen partial pressure detecting element.

Described in greater detail, the sensing element 10 has a planar body 12 which is made principally of an oxygen-ion conductive solid electrolyte such as zirconia containing yttria. In the interior of the above-indicated distal end portion of the planar solid electrolyte body 12, there is formed a circular thin flat space 14 which serves as diffusion-resistance means which has a predetermined diffusion resistance to the molecules of oxygen of a desired measurement gas. This circular thin flat space 14 communicates at its central portion, with a gas-inlet aperture 16 which is in turn held in communication with an external measurement-gas space in which the measurement gas exists. Thus, the external measurement gas is introduced into the circular thin flat space 14 through the gas-inlet aperture 16. The planar solid electrolyte body 12 further has an air passage 18 formed therein as reference-gas inlet means, such that the air passage 18 extends in the longitudinal direction of the planar body 12. This air passage 18 is open to the external atmosphere, at the proximal end portion (the other longitudinal end portion) of the planar solid electrolyte body 12, so that an ambient air may be introduced into the air passage 18, as a reference gas or reference atmosphere.

On portions of an outer surface of the distal end portion of the planar body 12 substantially made of a solid electrolyte, there are formed two separate outer pumping electrodes 20, 30 having a generally sectorial shape. These outer pumping electrodes 20, 30 are located adjacent to an opening of the gas-inlet aperture 16, such that the electrodes 20, 30 are disposed corresponding to diametrically opposite portions of the opening of the gas-inlet aperture 16. Aligned with the two outer pumping electrodes 20, 30 in a plane parallel to the plane of the planar body 12, there are formed two separate inner pumping electrodes 22, 32 such that the electrodes 22, 32 communicate with the circular thin flat space 14. One of the two inner pumping electrodes 22, 32, i.e., the inner pumping electrode 32 serves as a catalytic electrode. This catalytic electrode is formed with a rhodium layer, which is obtained by sintering a paste of rhodium applied by printing on the surface of the electrode 32. On one of opposite surfaces of a portion of the planar body 12 disposed between the circular thin flat space 14 and the air passage 18, there are formed two separate measuring electrodes 24, 34 such that these two electrodes 24, 34 communicate with the circular thin flat space 14. On the other surface of the above-indicated portion of the planar body 12, there are formed two separate reference electrodes 26, 36 such that these two electrodes communicate with the air passage 18, for exposure to substantially the same reference gas or atmosphere (i.e., ambient air).

In the NOx sensor having the sensing element 10 constructed as described above, the outer pumping electrode 20 and the corresponding inner pumping electrode 22 are connected through suitable conductive wires to an external pumping power source (not shown), so that a pumping current is applied between the outer and inner pumping electrodes 20, 22, whereby a well known oxygen pumping action takes place between the two pumping electrodes 20, 22. Concurrently, the corresponding measuring and reference electrodes 24, 26 cooperate to detect an electromotive force induced therebetween, due to a difference in oxygen concentration between the reference gas (ambient air) within the air passage 18, and an atmosphere within the thin flat space 14 which is varied by the pumping action of the pumping electrodes 20, 22. Thus, the pair of pumping electrodes 20, 22 and the planar solid electrolyte body 12 cooperate to constitute a first electrochemical oxygen pumping cell, while the pair of measuring and reference electrodes 24, 26 and the solid electrolyte body 12 constitute a first electrochemical oxygen sensing cell. These first electrochemical oxygen pumping and sensing cells provide the first electrochemical oxygen partial pressure detecting element indicated above.

Similarly, the other outer pumping electrode 30 and the other inner pumping electrode 32 are supplied with a pumping current applied from the external pumping power source through conductive wires, so that these pair of pumping electrodes 30, 32 also perform a known pumping action. However, since the inner pumping electrode 32 or catalytic electrode is coated with rhodium, nitrogen oxides (NOx) contained in the measurement gas introduced from the external measurement-gas space are subjected to a reducing reaction by rhodium. The oxygen whose volume in the introduced measurement gas is increased by decomposition of NOx due to the reducing action, is affected by the oxygen pumping action of the pumping electrodes 30, 32. Concurrently, the other measuring electrode 34 and the other reference electrode 36 cooperate to detect an electromotive force induced therebetween, due to a difference in oxygen concentration between the thus controlled atmosphere within the thin flat space 14, and the reference gas (ambient air) within the air passage 18. Thus, the above-indicated other pair of pumping electrodes 30, 32 and the solid electrolyte body 12 constitute a second electrochemical pumping cell, while the above-indicated other pair of measuring and reference electrodes 34, 36 and the solid electrolyte body 12 constitute a second electrochemical sensing cell. These second electrochemica pumping and sensing cells cooperate to provide the second electrochemical oxygen partial pressure detecting element indicated above.

A heating element 40 is embedded within an outer wall which partially defines the air passage 18 and which provides an outer surface opposite to the surface on which the outer pumping electrodes 20, 30 are formed. The heating element 40 is connected to a suitable external power source, so that the first and second electrochemical oxygen partial pressure detecting elements may be heated to and maintained at an optimum operating temperature.

In the NOx sensor having the thus constructed sensing element 10, the first electrochemical oxygen partial pressure detecting element (12, 14, 18, 20, 22, 24, 26) is adapted to detect the oxygen partial pressure (concentration) of the introduced measurement gas, while the second electrochemical oxygen partial pressure detecting element (12, 14, 18, 30, 32, 34, 36) is adapted to detect the oxygen partial pressure (concentration) of the measurement gas which contains the molecules of oxygen produced by decomposition of NOx due to a reducing reaction by rhodium of the catalytic inner pumping electrode 32. Generally, the concentration of the nitrogen oxides (NOx) contained in the measurement gas is determined by a difference between two output signals of the first and second detecting elements indicative of oxygen partial pressures, usually in the form of pumping currents (Ip).

An experiment was conducted on a specimen of the present NOx sensor, wherein the solid electrolyte body 12 was made of zirconia containing yttria, while the electrodes 20, 22, 24, 26, 30, 34, 36 were made of platinum. The inner pumping electrode 32 was formed by sintering an unfired platinum layer coated with a printed layer of a rhodium paste. Further, the heating element 40 was also formed of platinum. The specimen had the circular thin flat space 14 as diffusion-resistance means which has a thickness of 15 microns and a diameter of 3.5 mm. The gas-inlet aperture 16 formed in the specimen had a diameter of 0.8 mm and a length of 0.4 mm. The generally sectorial outer pumping electrodes 20, 30 had a width of 1 mm and a length of 2 mm. The result of the experiment will be described below.

Figure 4:
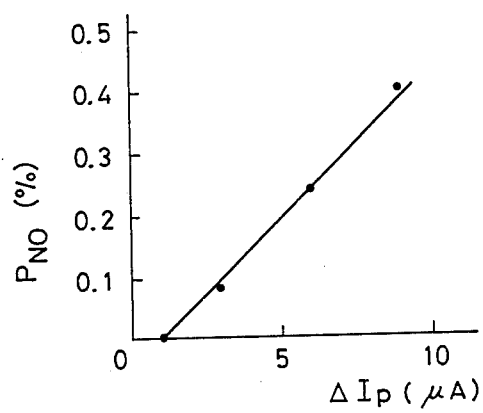
FIGS. 4 through 8 are graphs showing relationships between an output signal (difference between output signals) of the illustrated NOx sensors, and an NOx concentration of a measurement gas measured by the sensors.
Figure 5:
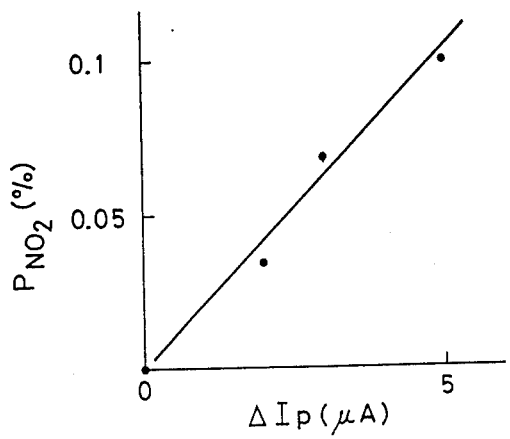

In the experiment, the sensing element 10 was exposed to a measurement gas while the element 10 was maintained at 500° C. by the energized heating element 40. The concentration of the nitrogen oxides (NO and $NO_2$) in the measurement gas was vaired to different levels. The obtained results are listed in Tables 1 and 2 given below. FIGS. 4 and 5 show relationships between the obtained output signals (difference $\Delta Ip$ between the two pumping currents Ip obtained from the first and second detecting elements) and the NOx concentration of the various measurement gases.

TABLE 1

| Gas Constituents | | | Sensor Outputs | | | |
|---|---|---|---|---|---|---|
| | | | First Detecting Element | | Second Detecting Element | |
| | | | (Pt electrode) | | (Rh electrode) | |
| $O_2$ (%) | NO (ppm) | CO (ppm) | Ip (mA) | $P_{O_2}$ (%) | Ip (mA) | $P_{O_2}$ (%) |
| 2.683 | 0 | 0 | 0.129 | 2.670 | 0.130 | 2.679 |
| 2.683 | 800 | 0 | 0.129 | 2.672 | 0.132 | 2.723 |
| 2.683 | 2410 | 0 | 0.130 | 2.678 | 0.136 | 2.804 |
| 2.683 | 4020 | 0 | 0.130 | 2.680 | 0.139 | 2.878 |

TABLE 2

| Gas Constituents | | Sensor Outputs | | | |
|---|---|---|---|---|---|
| | | First Detecting Element (Pt electrode) | | Second Detecting Element (Rh electrode) | |
| $O_2$ (%) | $NO_2$ (ppm) | Ip (mA) | $P_{O_2}$ (%) | Ip (mA) | $P_{O_2}$ (%) |
| 0.510 | 0 | 0.024 | 0.504 | 0.024 | 0.506 |
| 0.510 | 340 | 0.024 | 0.505 | 0.026 | 0.540 |
| 0.510 | 680 | 0.025 | 0.508 | 0.028 | 0.574 |
| 0.510 | 1020 | 0.025 | 0.510 | 0.030 | 0.610 |

As indicated in the relationships indicated in FIGS. 4 and 5, it will be easily understood that it is possible to determine the concentration of the NOx (NO and $NO_2$) based on the output signals (pumping currents Ip) produced by the NOx sensor.

In the present sensing element 10, only the inner pumping electrode 32 of the oxygen pumping cell of the second oxygen partial pressure detecting element is used as a catalytic electrode provided with rhodium. In the following experiment, however, the inner platinum pumping electrode 32 was not provided with rhodium but the measuring electrode 34 of the second oxygen sensing cell was used as a catalystic electrode, which was formed by sintering an unfired platinum layer coated with a printed layer of a rhodium paste.

Figure 6:
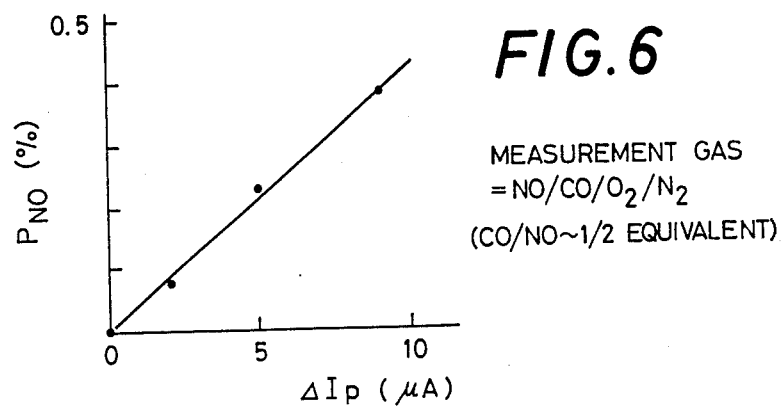

As in the preceding experiment, the specimen was exposed to a measurement gas, for measurement of NOx concentration, while the specimen was maintained at an elevated operating temperature by the heating element 40. In the present experiment, the concentration of nitric oxide or nitrogen monoxide (NO) in the measurement gas was varied, in the presence of CO (reducing gas). The pumping currents Ip obtained by the first and second detecting elements, and the oxygen partial pressures ($P_{O_2}$) are listed in Table 3. FIG. 6 shows a relationship between the output signals (difference $\Delta Ip$ between the two pumping currents Ip of the first and second detecting elements) and the NO concentration of the various measurement gases.

TABLE 3

| Gas Constituents | | | Sensor Outputs | | | |
|---|---|---|---|---|---|---|
| | | | First Detecting Element | | Second Detecting Element | |
| | | | (Pt electrode) | | (Rh electrode) | |
| $O_2$ (%) | NO (ppm) | CO (ppm) | Ip (mA) | $P_{O_2}$ (%) | Ip (mA) | $P_{O_2}$ (%) |
| 2.576 | 0 | 1940 | 0.120 | 2.480 | 0.120 | 2.479 |
| 2.576 | 770 | 1940 | 0.120 | 2.482 | 0.122 | 2.518 |
| 2.576 | 2310 | 1940 | 0.121 | 2.489 | 0.126 | 2.596 |
| 2.576 | 3860 | 1940 | 0.121 | 2.492 | 0.130 | 2.672 |

It will be easily understood from the graph of FIG. 6 that it is possible to determine the concentration of the nitrogen oxides based on the output signals (pumping currents) of the first and second oxygen partial pressure detecting elements, even when the measuement gases contain a reducing gas.

Figure 2A:
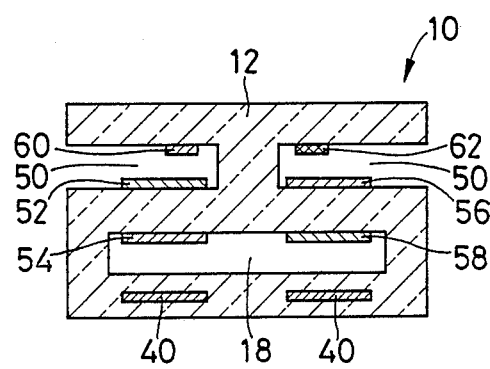
FIGS. 2(a) and 3(a) are elevational views in transverse cross section of sensing elements of other embodiments of the NOx sensor of the invention, corresponding to that of FIG. 1(a)
Figure 2B:
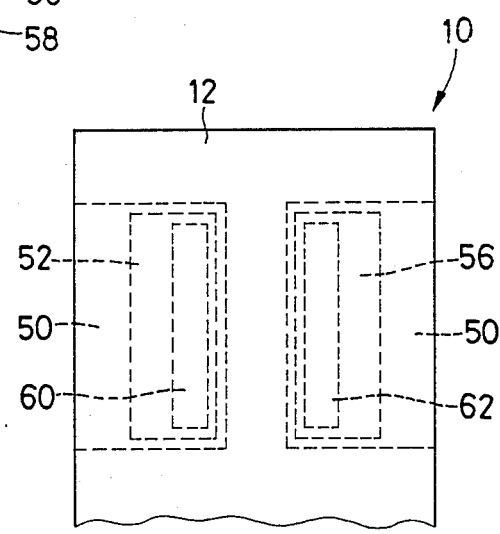
FIGS. 2(b) and 3(b) are fragmentary plan views of the sensing elements of FIGS. 2(a) and 3(a), corresponding to that of FIG. 1(b)

Referring next to FIGS. 2(a) and 2(b), there is shown a sensing element 10 used in another embodiment of the NOx sensor of the present invention, wherein the generally elongate planar body 12 having a relatively small width is substantially formed of a solid electrolyte such as zirconia, as in the preceding embodiment. In the present modified embodiment, the distal detecting end portion of the planar solid electrolyte body 12 has two diffusion-resistance slits 50, 50 having substantially the same diffusion resistance. Each of the slits 50 has a thickness of 15 microns, and a width of 3.5 mm as seen in FIG. 2(a).

On one of opposite surfaces of a portion of the planar solid electrolyte body 12 which separates the diffusion-resistance slits 50, 50 and the air passage 18 from each other, there are formed two separate pumping electrodes 52, 56 such that these electrodes communicate with the respective slits 50, 50. On the other surface of the above-indicated portion of the body 12, there are formed two separate reference-air electrodes 54, 58 such that these electrodes communicate with the air passage 18. These reference-air electrodes 54, 58 serve also as pumping electrodes. The electrodes 52, 56, 54 and 58 are all formed of platinum. Two oxygen partial pressure detecting electrodes 60, 62 are formed such that these electrodes face the pumping electrodes 52, 56, respectively, and commuunicate with the respectiveslits 50, 50. One of the oxygen partial pressure detecting electrodes 60, 62, i.e., the electrode 60 is formed of platinum, while the other oxygen partial pressure detecting electrode 62 is used as a catalystic electrode, which is formed by sintering an unfired platinum layer coated with a printed layer of a rhodium paste. Thus, the electrode 62 is coated with rhodium.

As is apparent from FIG. 2(b), the pumping electrodes 52, 56, and the oxygen partial pressure detecting electrodes 60, 62, have generally elongate rectangular shapes. Each of the pumping electrodes 52, 56 has a width of 1 mm and a length of 2 mm, while each of the detecting electrodes 60, 62 has a width of 0.5 mm and a length of 1.6 mm.

In the sensing element 10 of the present NOx sensor, the pumping electrode 52, the reference-air electrode 54, and the solid electrolyte body 12 constitute a first oxygen pumping cell, while the oxygen partial pressure detecting electrode 60, the reference-air electrode 54 and the body 12 constitute a first oxygen sensing cell. These first oxygen pumping and sensing cells provide the first oxygen partial pressure detecting element. On the other hand, the pumping electrode 56, the reference-air electrode 58 and the body 12 constitute a second oxygen pumping cell, while the oxygen partial pressure detecting electrode 62, the reference-air electrode 58 and the body 12 constitute a second oxygen sensing cell. The second oxygen pumping and sensing cells provide the second oxygen partial pressure detecting element.

The concentration of nitrogen monoxide (NO) in a measurement gas was measured by the instant NOx sensor whose sensing element 10 is constructed and dimensioned as described above. The NO concentration was varied in the presence of CO gas (reducing gas). Measurements of the NO concentration were obtained based on pumping currents (Ip) obtained from the first and second detecting elements as output signals indicative of the NO concentrations. The results are listed in Table 4 and a relationship between the output of the Nox sensor and the NO concentration of the measurement gases are shown in FIG. 7.

TABLE 4

| Gas Constituents | | | | Sensor Outputs | | | |
|---|---|---|---|---|---|---|---|
| | | | | First Detecting Element (Pt electrode) | | Second Detecting Element (Rh electrode) | |
| $O_2$ (%) | NO (ppm) | $NO_2$ (ppm) | CO (ppm) | Ip (mA) | $P_{O_2}$ (%) | Ip (mA) | $P_{O_2}$ (%) |
| 2.477 | 0 | 170 | 3460 | 0.168 | 2.301 | 0.169 | 2.322 |
| 2.477 | 690 | 170 | 3460 | 0.168 | 2.301 | 0.171 | 2.355 |
| 2.477 | 2060 | 170 | 3460 | 0.168 | 2.302 | 0.177 | 2.424 |
| 2.477 | 3440 | 170 | 3460 | 0.168 | 2.303 | 0.181 | 2.493 |

Figure 7:
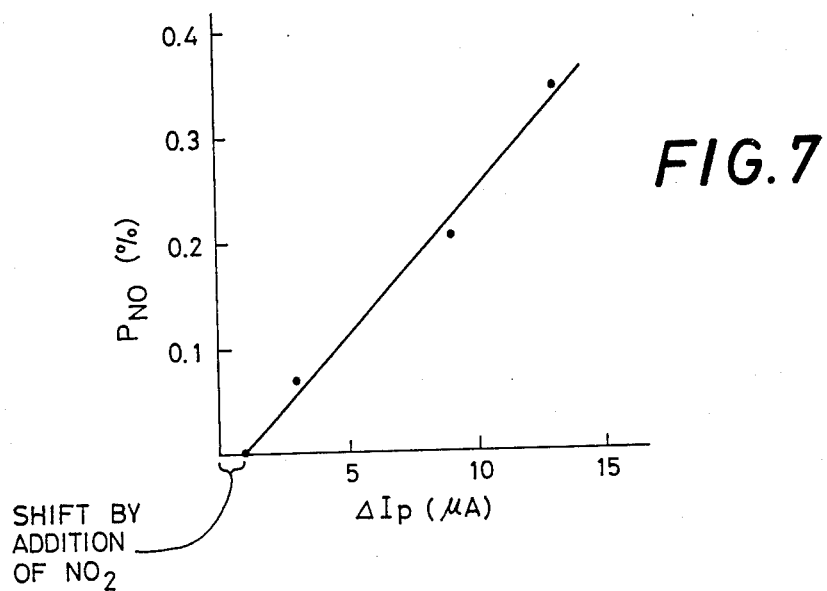

It will be easily understood from the graph of FIG. 7 that it is possible to determine the NOx concentration of the measurement gas, based on the obtained output signals (pumping currents) of the NOx sensor, even if the slits 50, 50 are used as modified diffusion-resistance means, and even when the measurement gas contains CO and $NO_2$.

An experiment was also conducted on a modified specimen wherein the pumping electrode 52 and the oxygen partial pressure detecting electrodes 60, 62 were formed of platinum, while the other pumping electrode 56 was used as a catalytic electrode formed from a platinum layer provided with rhodium. This modified NOx sensor showed a similar relationship between the obtained pumping current signals and the NOx concentration, to that obtained in the preceding embodiment wherein the oxygen partial pressure detecting electrode 62 is provided with rhodium.

Figure 3A:
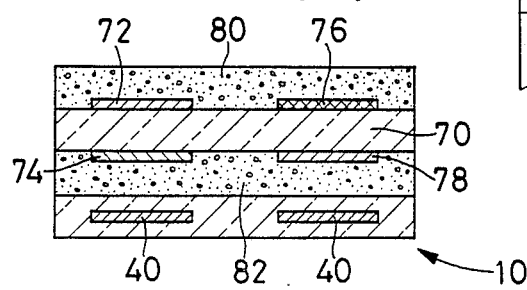
Figure 3B:
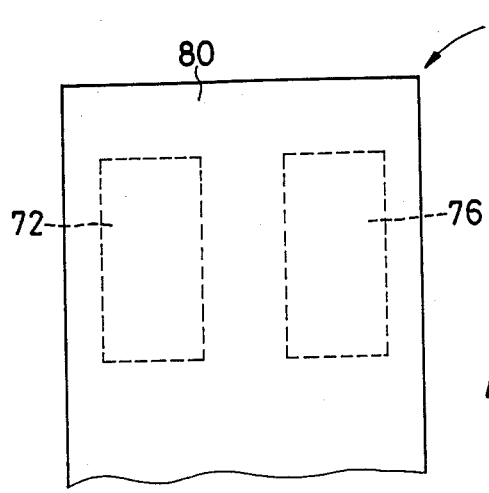

A further modified embodiment of the NOx sensor of the invention is illustrated in FIGS. 3(a) and 3(b). This sensor is characterized in that the first and second oxygen partial pressure detecting elements use a common oxygen pumping cell and a common oxygen sensing cell.

Described more specifically, the sensing element 10 uses a planar body 70 made of oxygen-ion conductive solid electrolyte such as zirconia. On one of opposite surfaces of the planar solid electrolyte body 12, there are formed two separate pumping electrodes 72, 76 which are covered by a diffusion-resistance layer (porous ceramic layer) 80 having a predetermined diffusion resistance. On the other surface of the planar solid electrolyte body 70, there are formed two separate pumping electrodes 74, 78 such that these electrodes are embedded in a porous ceramic layer 82 having a predetermined diffusion resistance. The pumping electrodes 72, 74 and 78 are made of platinum, while the other pumping electrode 76 is used as a catalytic electrode formed by sintering an unfired platinum layer coated with a printed layer of a rhodium paste.

In operation of the NOx sensor, the thus constructed sensing element 10 is exposed to a desired measurement gas while maintained at a suitable operating temperature by the energized heating element 40. Voltages are applied between the pumping electrodes 72 and 74, and between the pumping electrodes 76 and 78. As a result, diffusion limited current are induced between the pumping electrodes 72, 74, and between the pumping electrodes 76, 78, corresponding to the oxygen concentrations of the atmospheres adjacent to the pumping electrodes 72, 76, respectively. Namely, the limiting currents are obtained as output signals indicative of the oxygen partial pressures.

Figure 8:
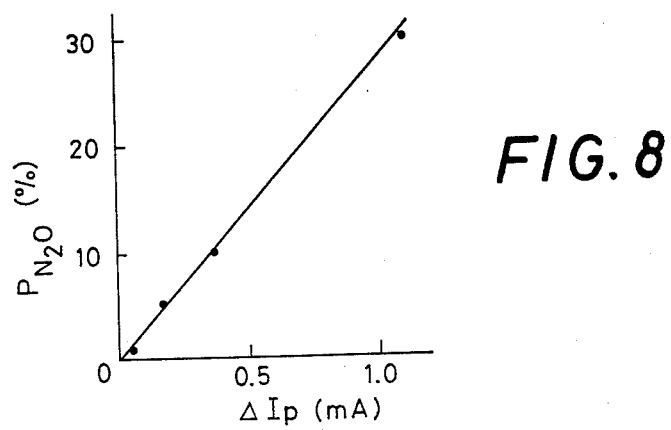

Table 5 lists the output values of the present NOx sensor obtained in the above manner, while the NOx ($N_2O$) concentration of the measurement gas was varied to different levels. The graph of FIG. 8 shows a relationship between the sensor outputs and the $N_2O$ concentration of the measurement gas. It will be easily understood that the concentration of nitrogen oxides ($N_2O$) can be determined based on the outputs (in the form of diffusion limited current).

TABLE 5

| Gas Constituents | | Sensor Outputs | | | |
|---|---|---|---|---|---|
| | | First Detecting Element (Pt electrode) | | Second Detecting Element (Rh electrode) | |
| $O_2$ (%) | $N_2O$ (ppm) | Ip (mA) | $P_{O_2}$ (%) | Ip (mA) | $P_{O_2}$ (%) |
| 20.0 | 1.0 | 1.748 | 20.0 | 1.791 | 20.5 |
| 20.0 | 5.0 | 1.774 | 20.3 | 1.948 | 22.3 |
| 20.0 | 10.0 | 1.791 | 20.5 | 2.158 | 24.7 |
| 20.0 | 30.0 | 1.879 | 21.5 | 2.988 | 34.2 |

The solid electrolyte body (12, 70) used in the present invention may be formed of any conductive solid electrolyte material having an oxygen-ion conductivity at an elevated temperature, as used in the known oxygen sensors utilizing an electrochemical reaction. For instance, the solid electrolyte body is formed of a solid solution of zirconia and calcia, a solid solution of zirconia and yttria or a solid solution of thoria and yttria. While the solid electrolyte body preferably has a generally planar configuration as in the illustrated embodiments, other configurations such as a tubular shape (like a test tube) may be suitably selected to meet specific requirements of the sensor.

As described above, the pumping electrodes, and measuring and reference electrodes (reference-air electrodes and oxygen partial pressure detecting electrodes) are formed in contacting engagement with the suitably shaped solid electrolyte body. These electrodes and their conductive leads are made principally of a metal such as platinum, palladium, iridium, ruthenium or osmium, as used in the known oxygen sensors. Preferably, the electrodes and their leads are co-fired with the solid electrolyte body. In this case, it is desired that the appropriate patterns of the electrodes and leads be printed on the unfired solid electrolyte body, with suitably prepared materials containing the selected metallic material as a major component, and subsequently co-fired with the solid electrolyte body. To avoid flake-off or peel-off, and/or disconnection of the electrodes and leads, it is advisable to add finely divided particles of a suitable ceramic material such as zirconia or alumina, to the materials of the electrodes and leads, so that the added powdered ceramic material improves the adhesion or bonding strength of the fired electrodes and leads to the contacting surfaces of the solid electrolyte.

As described above, one of the electrodes of the second oxygen partial pressure detecting element is used as a catalytic electrode which is provided with a catalyst for reducing nitrogen oxides, such that the electrode is coated or covered by a layer of rhodium, in the illustrated embodiments. According to the present invention, however, the NOx reducing catalyst may be applied to the electrode, by mixing the catalyst into the metallic material of the electrode so that the electrode is impregnated with the catalyst. Alternatively the catalyst may be applied by forming a layer of the catalyst on a suitable ceramic overcoat formed on the electrode, or by mixing the catalyst into the material of such a ceramic overcoat so that the overcoat is impregnated with the catalyst. In the case where the catalyst is provided as a layer, it is desired to add to the catalyst a finely powdered ceramic material as described above with respect to the electrodes, for improving the adhesion of the catalyst layer to the electrode or ceramic overcoat.

It is preferred that the sensing element of the NOx sensor according to the present invention be formed as a laminar structure, in a well known manner used for preparing a conventional oxygen sensor of a laminar type. Where the sensing element includes a porous solid electrolyte layer or ceramic layer, such porous layers may be formed by a known coating method. For instance, a porous layer serving as diffusion-resistance means may be applied by plasma coating method, to an appropriate one of separately prepared cell structures of the sensing element, or to an intergrally formed assembly of the cell structures.

Although it is desired to form the first and second electrochemical oxygen partial pressure detecting elements as an integrally formed one-piece element as in the illustrated embodiments, it is possible that the first and second elements are formed as separate pieces. While each of these first and second oxygen partial pressure detecting elements of the illustrated NOx sensors uses diffusion-resistance means in the form of a thin flat space or slit, or a porous layer, it is possible to use other forms of diffusion-resistance means. For example, the gas-inlet aperture 16 may be formed as a pin hole having a predetermined diffusion resistance. Certainly, the diameter of such a pin hole, the thickness of the thin flat space or slit, and the porosity and its distribution of the porous layer, may be suitably determined.

The electrochemical pumping and sensing cells of each of the first and second oxygen partial pressure detecting elements of the NOx sensor of the invention are preferably maintained at an elevated operating temperature by suitable heating means as provided in the illustrated embodiments, preferably by heating means capabale of controlling the temperature of the cells. To improve the measuring accuracy of the NOx sensor, it is desirable that the heater means is electrically insulated from the electrochemical cells, in particular, from the electrodes of the oxygen partial pressure detecting cells. However, the provision of such heating means is not essential to practice the present invention. Obviously, it is possible to pre-heat the measurement gas as in a pre-heating furnace, before the measurement gas is introduced into the sensing element. This pre-heating means is provided in place of, or in addition to, the heating means indicated above.

While the NOx sensor of the present invention has been described in its preferred embodiments, it is to be understood that the invention is by no means limited to the precise details of the illustrated construction of the preferred embodiments, but may be embodied with various changes, modifications and improvements, which may occur to those skilled in the art, in the light of the arrangements of the known oxygen sensors, without departing from the spirit and scope of the invention defined in the appended claims.

As described above, the NOx sensor constructed according to the present invention uses a sensing element including two electrochemical oxygen partial pressure detecting elements, wherein one of the oxygen partial pressure detecting electrodes or pumping electrodes of one of the two detecting elements is provided with a suitable catalyst such as rhodium for reducing nitrogen oxides contained in the measurement gas, so that the concentration of the nitrogen oxides (NOx) can be measured or determined based on the pumping currents (or diffusion limited current), without being influenced by a reducing gas such as CO even if contained in the measurement gas.

The NOx sensor constructed according to the invention may be suitably used as a sensor for detecting or determining nitrogen oxides (NOx) contained in exhaust emissions from an internal combustion engine, various burned exhaust gases emitted from heating furnaces or boilers, or anesthetic gases.

What is claimed is:

1. An NOx sensor for determining the concentration of nitrogen oxides contained in a measurement gas in an external measurement-gas space, comprising:
    a first electrochemical oxygen partial pressure detecting element including (a) a first electrochemical oxygen pumping cell having an oxygen-ion conductive solid electrolyte body, and a pair of electrodes, (b) a first electrochemical oxygen sensing cell having an oxygen-ion conductive solid electrolyte body, and a pair of electrodes, (c) first diffusion-resistance means for introducing said measurement gas from said external measurement-gas space, with a first predetermined diffusion resistance, so that one of said pair of electrodes of said first oxygen pumping cell, and one of said pair of electrodes of said first oxygen sensing cell, are exposed to the introduced measurement gas, and (d) first reference-gas inlet means for exposing the other of said pair of electrodes of said first oxygen sensing cell to a reference gas;

a second electrochemical oxygen partial pressure detecting element including (i) a second electrochemical oxygen pumping cell having an oxygen-ion conductive solid electrolyte body, and a pair of electrodes, (ii) a second electrochemical oxygen sensing cell having an oxygen-ion conductive solid electrolyte body, and a pair of electrodes, (iii) second diffusion-resistance means for introducing said measurement gas from said external measurement-gas space, with a second predetermined diffusion resistance substantially equal to said first predetermined diffusion resistance, so that one of said pair of electrodes of said second oxygen pumping cell, and one of said pair of electrodes of said second oxygen sensing cell, are exposed to the introduced measurement gas, and (iv) second reference-gas inlet means for exposing the other of said pair of electrodes of said second oxygen sensing cell to a reference atmosphere substantially the same as said reference gas;

at least one catalytic electrode which consists of at least one of said one electrode of said second oxygen pumping cell and said one electrode of said second oxygen sensing cell, which are exposed to a portion of the measurement gas introduced through said second diffusion-resistance means, said at least one catalytic electrode being provided with a catalyst for reducing nitrogen oxides contained in the introduced measurement gas, so that said second electrochemical oxygen partial pressure detecting element detects an oxygen partial pressure of the portion of the measurement gas introduced through said second diffusion-resistance means, while said nitrogen oxides are reduced by said catalyst; and means for determining the concentration of said nitrogen oxides based on a difference between two outputs of said first and second electrochemical oxygen partial pressure detecting elements, said two outputs representing the oxygen partial pressures of the respective portions of the measurement gas introduced through said first and second diffusion-resistance means.

2. An NOx sensor according to claim 1, wherein said catalyst consists of at least one material selected from the group consisting of rhodium, cobalt oxide, nickel oxide, palladium, cerium oxide and lanthanum oxide.

3. An NOx sensor according to claim 1, wherein said catalyst is applied to said at least one catalytic electrode such that said at least one catalytic electrode is impregnated with said catalyst.

4. An NOx sensor according to claim 1, wherein said catalyst is applied to said at least one catalytic electrode such that said at least one catalytic electrode is coated with a layer of said catalyst.

5. An NOx sensor according to claim 1, wherein said catalyst is applied to said at least one catalytic electrode such that said at least one catalytic electrode is coated with a ceramic overcoat, and a layer of said catalyst formed on said ceramic overcoat.

6. An NOx sensor according to claim 1, wherein said catalyst is applied to said at least one catalytic electrode such that said at least one catalytic electrode is coated with a ceramic overcoat which is impregnated with said catalyst.

7. An NOx sensor according to claim 1, wherein said first and second electrochemical oxygen partial pressure detecting elements consist of an integrally formed one-piece structure.

8. An NOx sensor according to claim 7, wherein said first and second diffusion-resistance means are defined by an integral portion of said integrally formed one-piece structure.

9. An NOx sensor according to claim 7, wherein said first and second reference-gas inlet means are defined by an integral portion of said integrally formed one-piece structure.

10. An NOx sensor according to claim 7, wherein at least one of said pair of electrodes of said first oxygen pumping cell is commonly used as at least one of said pair of electrodes of said first oxygen sensing cell.

11. An NOx sensor according to claim 7, wherein at least one of said pair of electrodes of said second oxygen pumping cell is commonly used as at least one of said pair of electrodes of said second oxygen sensing cell.

12. An NOx sensor according to claim 1, further comprising integrally formed heating means for heating said first and second oxygen pumping and sensing cells of said first and second electrochemical oxygen partial pressure detecting elements.

13. An NOx sensor for determining the concentration of nitrogen oxides contained in a measurement gas in an external measurement-gas space, comprising:

a first electrochemical oxygen partial pressure detecting element and a second electrochemical oxygen partial pressure detecting element, said first and second elements consisting of an integrally formed one piece structure;

said first electrochemical oxygen partial pressure detecting element including (a) a first electrochemical oxygen pumping cell having an oxygen-ion conductive solid electrolyte body, and a pair of electrodes, (b) a first electrochemical oxygen sensing cell having an oxygen-ion conductive solid electrolyte body, and a pair of electrodes, (c) first diffusion-resistance means for introducing said measurement gas from said external measurement-gas space, with a first predetermined diffusion resistance, so that one of said pair of electrodes of said first oxygen pumping cell, and one of said pair of electrodes of said first oxygen sensing cell, are exposed to the introduced measurement gas, and (d) first reference-gas inlet means for exposing the other of said pair of electrodes of said first oxygen sensing cell to a reference gas;

said second electrochemical oxygen partial pressure detecting element including (1) a second electrochemical oxygen pumping cell having an oxygen-ion conductive solid electrolyte body, and a pair of electrodes, (ii) a second electrochemical oxygen sensing cell having an oxygen-ion conductive solid electrolyte body, and a pair of electrodes, (iii) second diffusion-resistance means for introducing said measurement gas from said external measurement-gas space, with a second predetermined diffusion resistance substantially equal to said first predetermined diffusion resistance, so that one of said pair of electrodes of said second oxygen pumping cell, and one of said pair of electrodes of said second oxygen sensing cell, are exposed to the introduced measurement gas, and (iv) second reference-gas inlet means for exposing the other of said pair of electrodes of said second oxygen sensing cell to a reference atmosphere substantially the same as said reference gas;

at least one catalytic electrode which consists of at least one of said one electrode of said second oxygen pumping cell and said one electrode of said second oxygen sensing cell, which are exposed to a portion of the measurement gas introduced through said second diffusion-resistance means, said at least one catalytic electrode being provided with a catalyst for reducing nitrogen oxides contained in the introduced measurement gas, so that said second electrochemical oxygen partial pressure detecting element detects an oxygen partial pressure of the portion of the measurement gas introduced through said second diffusion-resistance means, while said nitrogen oxides are reduced by said catalyst;

means for determining the concentration of said nitrogen oxides based on a difference between two outputs of said first and second electrochemical oxygen partial pressure detecting elements, said two outputs representing the oxygen partial pressures of the respective portions of the measurement gas introduced through said first and second diffusion-resistance means; and heating means for heating said first and second oxygen pumping and sensing cells of said first and second electrochemical oxygen partial pressure detecting elements, said heating means being integrally formed with said one-piece structure.

14. An NOx sensor according to claim 13, wherein said catalyst consists of at least one material selected from the group consisting of rhodium, cobalt oxide, nickel oxide, palladium, cerium oxide and lanthanum oxide.

15. An NOx sensor according to claim 13, wherein said catalyst is applied to said at least one catalytic electrode such that said at least one catalytic electrode is impregnated with said catalyst.

16. An NOx sensor according to claim 13, wherein said catalyst is applied to said at least one catalytic electrode such that said at least one catalytic electrode is coated with a layer of said catalyst.

17. An NOx sensor according to claim 13, wherein said catalyst is applied to said at least one catalytic electrode such that said at least one catalytic electrode is coated with a ceramic overcoat, and a layer of said catalyst formed on said ceramic overcoat.

18. An NOx sensor according to claim 13, wherein said catalyst is applied to said at least one catalytic electrode such that said at least one catalytic electrode is coated with a ceramic overcoat which is impregnated with said catalyst.

19. An NOx sensor according to claim 13, wherein said first and second diffusion-resistance means are defined by an integral portion of said integrally formed one-piece structure.

20. An NOx sensor according to claim 13, wherein said first and second reference-gas inlet means are defined by an integral portion of said integrally formed one-piece structure.

21. An NOx sensor according to claim 13, wherein at least one of said pair of electrodes of said first oxygen pumping cell is commonly used as at least one of said pair of electrodes of said first oxygen sensing cell.

22. An NOx sensor according to claim 13, wherein at least one of said pair of electrodes of said second oxygen pumping cell is commonly used as at least one of said pair of electrodes of said second oxygen sensing cell.

* * * * *